United States Patent [19]
Good et al.

[11] Patent Number: 5,281,526
[45] Date of Patent: Jan. 25, 1994

[54] METHOD OF PURIFICATION OF AMYLASE BY PRECIPITATION WITH A METAL HALIDE AND 4-HYDROXYBENZIC ACID OR A DERIVATIVE THEREOF

[75] Inventors: Ivan C. Good, Goshen; Chong Y. Kim; Jayarama K. Shetty, both of Elkhart; Kent M. Sproat, Granger, all of Ind.

[73] Assignee: Solvay Enzymes, Inc., Elkhart, Ind.

[21] Appl. No.: 963,542

[22] Filed: Oct. 20, 1992

[51] Int. Cl.⁵ .......................... C12N 9/26; C12N 9/28
[52] U.S. Cl. ...................................... 435/202; 435/201
[58] Field of Search ...................... 435/206, 201, 202

[56] References Cited

U.S. PATENT DOCUMENTS

| | | | |
|---|---|---|---|
| 2,695,863 | 4/1952 | Tertrault et al. | 435/202 |
| 3,826,715 | 4/1972 | Horikoshi et al. | 435/202 |
| 4,642,288 | 2/1987 | De Miguel et al. | 435/202 |
| 4,659,667 | 4/1987 | Brewer et al. | 435/222 |
| 4,673,647 | 1/1987 | Brothers et al. | 435/202 |
| 4,676,986 | 1/1982 | Sills et al. | 435/202 |
| 4,717,662 | 1/1988 | Montgomery et al. | 436/202 |
| 5,041,377 | 8/1991 | Becker et al. | 435/220 |

FOREIGN PATENT DOCUMENTS

| | | | |
|---|---|---|---|
| 0140610 | 5/1985 | European Pat. Off. | 435/202 |
| 8905863 | 6/1989 | PCT Int'l Appl. | |
| WO91/09943 | 7/1991 | PCT Int'l Appl. | |

OTHER PUBLICATIONS

Horikoshi et al. *A New Microbial World*, Springer-Verlag, M.Y. pp. 93-143 (1981).
Starace et al. Encyclopedia of Chemical Technology, 9, 138-148 (1980).

*Primary Examiner*—Douglas W. Robinson
*Assistant Examiner*—Jeffrey J. Sevigny
*Attorney, Agent, or Firm*—Willian Brinks Hofer Gilson & Lione

[57] ABSTRACT

The present invention relates to a method for the preparation of a purified amylase recovered from a fermentation broth, by the addition of a precipitation agent which is a halide salt, most preferably sodium or potassium chloride. According to a preferred embodiment, a further precipitation agent is added which is an organic compound, most preferably an alkyl ester of 4-hydroxybenzoic acid.

The present invention also relates to the purified amylases so obtained and to the uses of these purified amylases.

20 Claims, No Drawings

METHOD OF PURIFICATION OF AMYLASE BY PRECIPITATION WITH A METAL HALIDE AND 4-HYDROXYBENZIC ACID OR A DERIVATIVE THEREOF

The present invention relates to the purification of amylase recovered from fermentation broths and to the purified amylase product that results therefrom.

BACKGROUND INFORMATION

The color and odor of amylases, i.e. of enzymes which catalyze the hydrolysis of starch, can adversely affect the quality of the therapeutic compositions and of the detergent formulations in which they are incorporated.

It is thus desirable that amylase preparations for detergent applications, pharmaceutical applications and food applications be free from components which can cause undesirable color and odor, as well as undesirable haze, instability and allergic activity in the final product. These components may be derived from the microorganisms themselves or from residual fermentation raw materials. In preparations of Gram positive Bacilli, cell wall anionic polymers, peptidoglycans, galactosyl polymers, and other polysaccharide contaminants become solubilized during cell growth due to cell wall turnover. The presence of these bacterial cell wall polymers in amylase preparations can cause several undesirable effects including an increase in the allergenicity, a decrease in amylase stability by binding cations, e.g., $Ca^{++}$, and may cause haze formation in detergent formulations. Therefore, it is essential to purify amylases recovered from fermentation broth.

U.S. Pat. No. 5,041,377 discloses a method of producing crystalline subtilisin, i.e. proteases, derived from *Bacillus subtilis* and *Bacillus amyloliquefaciens* by the addition of a halide salt to an alkaline subtilisin solution at temperatures less than 10° C., whereby halide salts comprise chlorides, bromides, iodides and fluorides of sodium, potassium or calcium and preferably sodium and calcium chloride.

PCT application WO 91/09943 discloses a method for crystallization of enzymes, such as an amylase, by means of a crystallization agent which is an easily soluble salt of the non-halide type, such as Na, K, Ca, or Mg formate, acetate or nitrate, is added to the aqueous enzyme.

U.S. Pat. No. 4,659,667 discloses a process for producing crystalline alpha-amylase enzyme by concentrating to supersaturation the alpha-amylase solution at a pH in a range near the isoelectric point of the enzyme. However supersaturated solutions are unstable and have to be treated with great care avoiding shocks, dust particles or scratches on the inner wall of the solution's containers. Moreover once the crystallization has been induced by stirring, incubation times of around 72 hours are necessary in order to have approximately 85%–86% of the amylase being in crystallized form.

SUMMARY OF THE INVENTION

It is an object of this invention to provide for a novel method of purifying amylases so as to remove pigments and other contaminants causing haze, color contamination and odor in commercial amylase preparations.

It is a further object of this invention to provide for a simple and novel method for the purification of amylases which removes polysaccharides and oligosaccharides and other galactosyl polymers which are responsible for problems associated with allergenic activity.

It is a further object of this invention to achieve the aforementioned objects through a novel method that is both simple, efficient and cost effective, yet results in a high recovery of pure amylase.

An advantage of one embodiment of the present invention is that, for the first time, a method of amylase purification is disclosed wherein the amylase is precipitated by compounds that also preserve and stabilize the amylase.

The method of the present invention eliminates many problems associated with the typical industrial amylase-containing liquid products, such as product stability, microbial contamination, large volume and high transportation costs.

The invention, together with further objects and attendant advantages, will best be understood by reference to the description, examples and tables herein. However, the invention is not limited thereto.

DETAILED DESCRIPTION

The present invention relates to a method for the preparation of purified amylase from a fermentation broth, comprising the following steps:
 (i) forming an amylase solution by separating the amylase from cells and suspended solids of said fermentation broth,
 (ii) concentrating said amylase solution into a concentrated amylase solution, until the enzyme activity of said concentrated amylase solution is at least about 250,000 MWU/ml,
 (iii) adding a precipitation agent to said concentrated amylase solution in an amount effective to precipitate the amylase, wherein said precipitation agent is a metal halide selected from the group consisting of alkali metal chlorides, alkali metal bromides and blends of two or more of these metal halides,
 (iv) incubating said concentrated amylase solution containing the precipitation agent during a time effective to precipitate the amylase, and
 (v) collecting a purified amylase precipitate.

By amylase we understand enzymes that catalyze the hydrolysis of starch, as well as protein engineered variants of amylases. The method of this invention applies to amylases such as alpha-amylases, alpha-1,4-glucano hydrolases, beta-amylases, glucoamylases, isoamylases, amyloglycosidases, transglucosylases, pullulanases, alpha-1,6-glucano hydrolases or amyloglucosidases. Usually the amylase is a bacterial amylase. In a preferred embodiment of the invention the amylase is an alpha-amylase or a protein engineered variant thereof and more preferably a bacterial alpha-amylase or a protein engineered variant of this amylase. In a more preferred embodiment the amylase is a bacterial alpha-amylase derived from a Bacillus species, such as amylases derived from *Bacillus licheniformis, Bacillus alcalophilus, Bacillus lentus, Bacillus amyloliquefaciens, Bacillus subtilis, Bacillus stearothermophilus*, their derivatives or a protein engineered variant of these amylases. Good results have been obtained with alpha-amylase derived from *Bacillus licheniformis*.

By purified amylase we understand an amylase enzyme having a substantially reduced color, as well as a substantially reduced content of carbohydrate polymers such as galactosyl polymer. With regards to reduced colors we understand thereby an amylase having an absorbance of less than 0.5 at 470 nm when the enzyme activity is adjusted to 100,000 MWU/ml, preferably an absorbance of less than 0.1 and more preferably of less than 0.09. With regard to reduced content of carbohydrate polymers, we understand thereby an amylase having a carbohydrate polymer content of less than 1.00 mg/kg of enzyme protein, when the enzyme activity is adjusted to 100,000 MWU/ml, preferably less than 0.65 mg/kg and more preferably less than 0.5 mg/kg.

Fermentation, separation, and concentration techniques are well known in the art and conventional methods can be used to achieve steps (i) and (ii) in order to prepare the concentrated amylase solution.

After fermentation, a fermentation broth is obtained, the microbial cells and various suspended solids, including residual raw fermentation materials, are removed by conventional separation techniques in order to obtain an amylase solution. Filtration, centrifugation, microfiltration, rotary vacuum filtration, ultrafiltration, centrifugation followed by ultra-filtration or the like are generally used. In the preferred embodiment of the invention centrifugation or ultrafiltration are used.

It is desirable to concentrate the amylase solution in order to optimize recovery. Use of unconcentrated solutions will require increased incubation time in order to collect the purified amylase precipitate.

The amylase solution is concentrated into a concentrated amylase solution using conventional concentration techniques until the desired enzyme activity is obtained. Concentration of amylase solution may be achieved by any of a variety of conventional techniques including filtration, centrifugation, rotary vacuum evaporation, ultrafiltration, extraction or chromatography. In the preferred embodiment of the invention rotary vacuum evaporation and/or ultrafiltration is used. In the most preferred embodiment of the invention ultrafiltration is used.

The amylase solution is concentrated into a concentrated amylase solution until the enzyme activity of said concentrated amylase solution is at least about 250,000 MWU/ml, preferably at least about 300,000 MWU/ml and more preferably at least about 350,000 MWU/ml. The best results have been obtained with an enzyme activity of at least about 450,000 MWU/ml.

By precipitation agent we understand a compound effective to precipitate the amylase from the concentrated amylase solution in solid form, whatever its nature may be, i.e. crystalline, amorphous or blend of both.

The metal halide precipitation agent is selected from the group consisting of alkali metal chlorides, alkali metal bromides and blends of two or more of these metal halides. Preferably the metal halide is selected from the group consisting of sodium chloride, potassium chloride, sodium bromide, potassium bromide and blends of two or more of these metal halides. More preferably the metal halide is chosen from amongst sodium chloride and potassium chloride, the most prefered metal halide precipitation agent being sodium chloride which is furthermore a preservative agent of amylases.

The metal halide precipitation agent is used in an amount effective to precipitate the amylase. The selection of at least an effective amount and an optimum amount of metal halide effective to cause precipitation of the amylase according to the invention, as well as the conditions of the precipitation for maximum recovery including incubation time, pH, temperature and concentration of amylase, will be readily apparent to one of ordinary skill in the art, in light of the present disclosure, after simple routine testing.

Generally at least 5% w/v (weight/volume) of metal halide is added to the concentrated amylase solution and usually at least 8% w/v. Generally no more than 25% w/v (weight/volume) of metal halide is added to the concentrated amylase solution and usually no more than 20% w/v.

The optimal concentration of the metal halide precipitation agent will depend, among others, on the nature of the specific amylase and on its concentration in the concentrated amylase solution.

According to an alternative and most preferred embodiment of the present invention, a further precipitation agent, which is an organic compound, is added to the concentrated amylase solution at step (iii). Thus, step (iii) preferably further comprises adding to the concentrated amylase solution a further precipitation agent which is an organic compound selected from the group consisting of 4-hydroxybenzoic acid, alkali metal salts of 4-hydroxybenzoic acid, alkyl esters of 4-hydroxybenzoic acid and blends of two or more of these organic compounds. The addition of said organic compound precipitation agents can take place prior to, simultaneously with or subsequent to the addition of the metal halide precipitation agent, and the addition of both precipitation agents, organic compound and metal halide, may be carried out sequentially or simultaneously.

Addition of the said organic compound precipitation agent provides the unexpected advantage of high flexibility of the precipitation conditions with respect to pH, temperature, amylase concentration, precipitation agent concentration and time of incubation.

Suitable organic compounds usuable as precipitation agents are selected from the group consisting of 4-hydroxybenzoic acid, alkali metal salts of 4-hydroxybenzoic acid, alkyl esters of 4-hydroxybenzoic acid and blends of two or more of these organic compounds. Generally the organic compound precipitation agents are selected from the group consisting of alkali metal salts of 4-hydroxybenzoic acid, such as sodium or potassium salts, and linear or branched alkyl esters of 4-hydroxybenzoic acid, wherein the alkyl group contains from 1 to 12 carbon atoms, and blends of two or more of these organic compounds. Preferably they are selected from the group consisting of linear or branched alkyl esters of 4-hydroxybenzoic acid, wherein the alkyl group contains from 1 to 10 carbon atoms, and blends of two or more of these organic compounds. More preferably the organic compounds are selected from the group consisting of linear alkyl esters of 4-hydroxybenzoic acid, wherein the alkyl group contains from 1 to 6 carbon atoms, and blends of two or more of these organic compounds. Examples of more preferred organic compounds are methyl ester of 4-hydroxybenzoic acid, propyl ester of 4-hydroxybenzoic acid, butyl ester of 4-hydroxybenzoic acid, ethyl ester of 4-hydroxybenzoic acid and blends of two or more of these organic compounds. Among them the most preferred ones are 4-hydroxybenzoic acid methyl ester (named methyl PARABEN), 4-hydroxybenzoic acid propyl ester (named propyl PARABEN), which are both excellent preservative agents of amylases.

The organic compound precipitation agent is used in an amount effective to improve precipitation of the amylase by means of the metal halide precipitation agent. The selection of at least an effective amount and an optimum amount of organic compound precipitation agent, as well as the conditions of the precipitation for maximum recovery including incubation time, pH, temperature and concentration of amylase, will be readily apparent to one of ordinary skill in the art, in light of the present disclosure, after simple routine testing.

Generally at least 0.01% w/v (weight/volume) of organic compound precipitation agent is added to the concentrated amylase solution and usually at least 0.02% w/v. Generally no more than 0.3% w/v (weight/volume) of organic compound precipitation agent is added to the concentrated amylase solution and usually no more than 0.2% w/v.

The concentrated amylase solution, containing the metal halide precipitation agent and, in the most preferred embodiment of the invention, the organic compound precipitation agent, is adjusted to a pH which will, of necessity, depend on the amylase to be purified. Generally the pH is adjusted at a level near the isoelectic point of the amylase. Preferably the pH is adjusted at a pH in a range from about 2.5 pH units below the isoelectric point up to about 2.5 pH units above the isoelectric point. For purposes of illustration, when the amylase is an alpha-amylase derived from *Bacillus licheniformis*, the concentrated amylase solution is usually adjusted to a pH of between about 5.5 and 9.7 and preferably to a pH of between about 6.5 and 9.0.

The time of incubation necessary to obtain a purified amylase precipitate according to the present invention will not only depend on the nature of the specific amylase and its concentration but also on the nature of the specific precipitation agent(s) and its (their) concentration. Generally the time effective to precipitate the amylase during step (iv) is between about 1 to 30 hours. Usually it does not exceed 25 hours. In the presence of the organic compound precipitation agent the time of incubation can still be reduced, and it does not exceed 10 hours and in most cases even 6 hours.

Generally the temperature during incubation is between about 4° C. and about 50° C. Usually the method is carried out at a temperature between about 10° C. and about 45° C., and preferably between about 20° C. and about 40° C. The optimal temperature for inducing precipitation will vary according to the solution conditions and the amylase or precipitation agent(s) used.

The overall recovery of purified amylase precipitate and the efficiency with which the process is conducted will be improved by agitating the solution comprising the amylase, the added metal halide and the added organic compound, both during addition of the metal halide and the organic compound and during the subsequent incubation period. Suitable agitation methods include mechanical stirring or shaking, vigourous aeration or any similar art recognized technique.

After the incubation period, the purified amylase is then separated from the dissociated pigment and other impurities and collected by conventional seperation techniques, such as filtration, centrifugation, microfiltration, rotary vacuum filtration, ultrafiltration, press filtration, cross membrane microfiltration, cross flow membrane microfiltration or the like. In the preferred embodiment of the invention filtration is used. Cross membrane microfiltration has been utilized for this purpose with excellent results. Further purification of the purified amylase precipitate can be obtained by washing the precipitate with water: so the method according to the invention preferably comprises after the step (v) the step (vi) consisting in washing the purified amylase precipitate with water. Preferably the purified amylase precipitate is washed with water containing the metal halide precipitation agent and more preferably with water containing the metal halide and the organic compound precipitation agents.

Purified amylases prepared according to the process of the present invention are useful for all applications in which amylases are generally utilized. For example they can be used in laundry detergents and spot removers, in the food industry, in starch processing and baking and in pharmaceutical compositions as digestive aids. They can be made into a final product that is either liquid (solution, slurry) or solid (granular, powder).

In the detergent applications, amylases prepared according to the invention are usually used in a liquid composition containing propylene glycol. The amylase is solubilized preferably in propylene glycol by circulating in a 25% volume/volume propylene glycol solution containing 10% calcium chloride. In the pharmaceutical applications amylases prepared according to the present invention are usually dried. Preferably they are dried by lyophilisation.

The following examples are intended to further illustrate the invention. It will be understood, however, that the invention is not limited to these specific examples or the embodiments expressed therein.

EXAMPLE 1

This example illustrates the effect of sodium chloride concentrations on alpha-amylase precipitation.

A fermentation broth is produced in a submerged culture of *Bacillus licheniformis* in a suitable medium, such as described in the U.S. Pat. No. 4,659,667.

After fermentation, an alpha-amylase enzyme solution is formed by separating the enzyme from the microbial cells, suspended solids, and other residual fermentation raw material, using centrifugation and vacuum drum filtration.

A concentrated amylase solution is then formed by the resultant alpha-amylase solution by ultrafiltration (UF) to an enzyme activity of 1,000,000 MWU/ml.

Sodium chloride is added at varying concentrations to the concentrated amylase solution according to table 1.

After complete solubilization of the sodium chloride, the pH of the concentrated amylase solution is adjusted to 7.6 using 10% sodium hydroxide.

The treated samples are then incubated at 25° C. under constant agitation by stirring with a magnetic stirrer.

After incubation for 24 hours, the amylase precipitate is separated by centrifugation at 15,000 rpm for 30 minutes.

The precipitate is then solubilized in 70% propylene glycol.

The percentage recovery of the purified alpha-amylase precipitate is measured by the determination of the enzyme activity of the composition so obtained.

Enzyme activity is determined based on the modified Wohlgemuth Units per milliliter (MWU/ml).

The amylase activity is measured using hydrolysis of soluble starch using blue value reduction of starch-iodine complex according to the Wohlgemuth method. In a typical run, 5 ml of 2% soluble starch buffered at a pH of 5.4 and 4 ml water are incubated with 1 ml properly diluted amylase in a water bath maintained at 40° C. At timed intervals (5-30 minutes from the addition of amylase) aliquots (1 ml) are withdrawn and injected into a tube containing 5 ml of dilute iodine solution and mixed by inversion. The developed color is then compared in a comparator to monitor the approach of the reaction end point. The enzyme activity is calculated as Modified Wohlgemuth Units per milliliter (MWU/ml).

One Modified Wohlgemuth Unit is that activity which dextrinizes one ml of soluble starch to a defined blue value in thirty minutes under the conditions of the assay. For the calculations it is assumed the density is that of water, and thus activity per milliliter is assumed to be equivalent to activity per gram. The calculation is:

$$MWU/ml = MWU/g = \frac{100 \times 30}{T \times W} = \frac{3000}{T \times W}$$

where
- 100 = milligram starch in each incubation mixture
- 30 = defined dextrinizing time in minutes
- T = time in minutes required to reach end point
- W = weight in grams of enzyme added to incubation mixture in one milliliter aliquot of enzyme dilution.

The total amylase activity value of the supernatant solution is compared to the activity of a non-precipitated control to determine the percentage recovery in the precipitate.

The effect of sodium chloride concentration on the amount of amylase precipitate is shown in table 1.

TABLE 1

Recovery of purified alpha-amylase precipitate using sodium chloride

| sodium chloride concentration % (weight/volume) | Percent recovery in purified precipitate % |
|---|---|
| 0 | 4.1 |
| 5 | 85.4 |
| 10 | 89.4 |
| 12 | 92.0 |
| 15 | 93.0 |

The purified alpha-amylase so obtained has a substantially reduced color due to the removal of pigment, it has an absorbance of about 0.08 at 470 nm when the enzymatic activity is adjusted to 100,000 MWU/ml. For comparison, the unpurified alpha-amylase has an absorbance of about 0.72 in the same conditions.

The purified alpha-amylase so obtained has a substantially reduced content of galactosyl polymer, it has a galactosyl polymer content of about 0.3 mg/kg of enzyme protein solution when the enzymatic activity is adjusted to 100,000 MWU/ml. For comparison, the unpurified alpha-amylase has a galactosyl polymer content of about 1985 mg/kg in the same conditions.

EXAMPLE 2

This example illustrates the effect of pH on alpha-amylase precipitation by means of sodium chloride.

A concentrated enzyme solution of alpha-amylase from *Bacillus licheniformis* with an activity of 1,000,000 MWU/ml, obtained according to the conditions of the example 1, is prepared.

12% of sodium chloride is added to this concentrated amylase solution. The pH of the separate aliquots of solution is adjusted to pH 6.0, 7.0, 7.6 and 8.0 with sodium hydroxide.

After stabilizing the pH, the treated samples are incubated at 25° C. for 24 hours with constant agitation by stirring. The amylase precipitates are separated by centrifugation (15,000 rpm 30 minutes) and the enzyme activity is measured to determine the percent recovery.

Results are shown in table 2.

TABLE 2

Effect of pH on purification of alpha-amylase

| pH during incubation | Percent recovery in precipitate % |
|---|---|
| 6.0 | 2.2 |
| 7.0 | 88.0 |
| 7.6 | 91.5 |
| 8.0 | 90.9 |

As shown in table 2, maximum precipitation of the alpha-amylase occurs in the neutral and basic pH ranges.

EXAMPLE 3

This example illustrates the use of sodium chloride and of 4-hydroxybenzoic acid methyl ester to precipitate alpha-amylase.

A concentrated enzyme solution of alpha-amylase from *Bacillus licheniformis* with an activity of 480,000 MWU/ml, obtained according to the conditions of the example 1, is prepared.

The pH of the concentrated amylase solution is adjusted to pH 7.0.

18% weight/volume of solid sodium chloride is added to the concentrated amylase solution. Then 0.12% (weight/volume) of 4-hydroxybenzoic acid methyl ester, named commonly methyl PARABEN, is added to the concentrated amylase solution containing NaCl.

The samples are then continuously stirred using magnetic stirrer at 37° C.

The samples are then withdrawn at different intervals of time, centrifuged to separate the precipitated amylase at 15,000 rpm for 30 minutes. The precipitated amylase is dissolved in propylene glycol.

The enzyme activity is measured to determine the percent recovery.

Results are shown in table 3.

TABLE 3

| Time of incubation hours | Percent recovery in precipitate % |
|---|---|
| 1 | 92.9 |
| 2 | 93.8 |
| 3 | 94.3 |
| 4 | 94.3 |

In the presence of sodium chloride and 4-hydroxybenzoic acid methyl ester, one hour of incubation is sufficient to allow precipitation of the alpha-amylase and to recover about 93% of the enzyme.

EXAMPLE 4

This example illustrates the effect of temperature on the precipitation of alpha-amylase by means of sodium chloride and 4-hydroxybenzoic acid methyl ester.

A concentrated enzyme solution of alpha-amylase from *Bacillus licheniformis* with an activity of 473,000 MWU/ml is prepared. Sodium chloride (18% weight/volume) and 4-hydroxybenzoic acid methyl ester (0.12% weight/volume) are added.

The pH of the solution is adjusted to a pH of 7.0 and the solution is incubated at varying temperatures for 4 hours with constant stirring. The precipitated amylase is separated by centrifugation at 15,000 rpm for 30 minutes. The precipitated amylase is dissolved in propylene glycol.

The enzyme activity is measured to determine the percent recovery.

Results are shown in table 4.

TABLE 4

| temperature of incubation °C. | percent recovery in precipitate % |
|---|---|
| 5 | 86.5 |
| 22 | 94.9 |
| 37 | 95.0 |

As shown in table 4, substantial precipitation occurs between 5° C. and 40° C. under these conditions and optimum precipitation occurs between about 20° and 40° C.

EXAMPLE 5

This example illustrates the effect of different concentrations of 4-hydroxybenzoic acid methyl ester on the precipitation of alpha-amylase by means of sodium chloride.

A concentrated enzyme solution of alpha-amylase from *Bacillus licheniformis* with an activity of 480,000 MWU/ml is prepared. 18% w/v of sodium chloride is added at the concentrated alpha-amylase solution. The pH is adjusted at pH 7.0 using sodium hydroxide.

4-hydroxybenzoic acid methyl ester is added to the concentrated amylase solution to different concentrations.

The solutions are incubated at 37° C. for 4 hours under constant agitation by stirring.

The amylase precipitates are separated by centrifugation and the precipitates are dissolved in propylene glycol. The enzyme activity is measured to determine the percent recovery.

Results are shown in table 5.

TABLE 5

| Effect of 4-hydroxybenzoic acid methyl ester concentration on amylase precipitation | |
|---|---|
| 4-hydroxybenzoic acid methyl ester concentration % w/v | percent recovery in precipitate % |
| 0 | 75 |
| 0.03 | 88.2 |
| 0.03 | 91.7 |
| 0.09 | 93.3 |
| 0.42 | 93.8 |

As shown in table 5, precipitation is much more effective in the presence of 4-hydroxybenzoic acid methyl ester in a quantity as low as 0.03% w/v under the conditions of this assay.

EXAMPLES 6, 7 and 8

This example illustrates the effect of 4-hydroxybenzoic acid methyl ester and of 4-hydroxybenzoic acid propyl ester on alphamylase precipitation by means of sodium chloride.

A concentrated enzyme solution of alpha-amylase from *Bacillus licheniformis* with an activity of 480,000 MWU/ml is prepared. 18% w/v of sodium chloride is added to the concentrated amylase solution (example 6).

Then 4-hydroxybenzoic acid methyl ester (0.12% w/v) is added to the concentrated amylase solution containing NaCl (example 7).

Then 4-hydroxybenzoic acid propyl ester (0.06% w/v) is added to the concentrated amylase solution containing NaCl 4-hydroxybenzoic acid methyl ester (example 8).

The pH is adjusted to pH 7.0 using sodium hydroxyde.

The solutions are incubated at 37° C. for 4 hours under constant agitation by stirring.

The amylase precipitates are separated by centrifugation and the enzyme activity is measured to determine the percent recovery.

Results are shown in table 6.

TABLE 6

| Examples | percent recovery in precipitate % |
|---|---|
| 6 | 76 |
| 7 | 94.8 |
| 8 | 95.6 |

As shown in table 6 addition of 4-hydroxybenzoic acid methyl ester and 4-hydroxybenzoic acid propyl ester increases the percent recovery of the alpha-amylase.

EXAMPLE 9

This example illustrates the effect of pH on the alpha-amylase precipitation by means of sodium chloride, 4-hydroxybenzoic acid methyl ester and 4-hydroxybenzoic acid propyl ester.

A concentrated enzyme solution of alpha-amylase from *Bacillus licheniformis* with an activity of 480,000 MWU/ml is prepared. Sodium chloride (18% w/v), 4-hydroxybenzoic acid methyl ester (0.12% w/v) and 4-hydroxybenzoic acid propyl ester (0.06% w/v) are added to the concentrated amylase solution.

The pH of the separate aliquots is adjusted to pH 6.5, 7.0, 7.5, 8.0 and 8.5 using sodium hydroxide.

The solutions are incubated at a temperature of 37° C. for 4 hours under constant agitation by stirring.

The amylase precipitates are separated by centrifuging at 15,000 rpm for 30 minutes from the supernatant.

The enzyme activity is measured to determine the percent recovery.

Results are shown in table 7.

TABLE 7

| Effect of pH on the amylase precipitation. | |
|---|---|
| pH | percent recovery in precipitate % |
| 6.5 | 94.3 |
| 7.0 | 95.8 |
| 7.5 | 95.6 |
| 8.0 | 95.0 |
| 8.5 | 92.3 |

As shown in table 7 maximum precipitation occurs at a pH in the range of about 6.5 through about 8.0.

Comparison of results in table 2 and table 7 shows that the addition of 4-hydroxybenzoic acid alkyl ester during precipitation of alpha-amylase by sodium chloride in the acidic pH results in a marked increase in the yield.

EXAMPLES 10 AND 11

These examples illustrate the effect of enzyme concentration rate of the concentrated amylase solution on alpha-amylase precipitation by sodium chloride and by sodium chloride containing 4-hydroxybenzoic acid methyl ester.

Different concentrated enzyme solutions of alpha-amylase from *Bacillus licheniformis* with different enzyme activity are prepared: 200,000 to 1,000,000 MWU/ml.

To one set of concentrated amylase solution (example 10) sodium chloride is added in a concentration of 12% w/v. To another set (example 11) sodium chloride (12% w/v) and 4-hydroxybenzoic acid methyl ester (0.12% w/v) are added.

The pH of the separate aliquots is adjusted to pH 7.6 using sodium hydroxide.

The solutions are incubated at a temperature of 25° C. for 24 hours under constant agitation by stirring.

The amylase precipitates are separated by centrifuging at 15,000 rpm for 30 minutes from the supernatant. The amylase precipitates are then dissolved in propylene glycol.

The enzyme activity is measured to determine the percent recovery.

Results are shown in table 8.

TABLE 8

| concentrated amylase solution enzyme activity MWU/ml | percent recovery in precipitate % | |
|---|---|---|
| | NaCl example 10 | Nacl + 4-hydroxybenzoic acid methyl ester example 11 |
| 200,000 | 0 | 0 |
| 350,000 | 0 | 82.3 |
| 500,000 | 67.4 | 90.8 |
| 750,000 | 83.9 | 93.3 |
| 1,000,000 | 91.4 | 98.5 |

As shown in table 8, 4-hydroxybenzoic acid methyl ester is effective to enhance the precipitation of alpha-amylase by sodium chloride at low concentration of the amylase enzyme.

EXAMPLES 12 AND 13

These examples illustrate the alpha-amylase precipitation by means of potassium chloride.

A concentrated enzyme solution of alpha-amylase from *Bacillus licheniformis* with an activity of 1,000,000 MWU/ml, obtained according to the conditions of the example 1, is prepared.

The pH of the concentrated amylase solution is adjusted to pH 7.6.

In example 12, potassium chloride is added to a concentration of 2M and in example 13, 4-hydroxybenzoic acid methyl ester is also added to a concentration of 0.12% w/v.

The samples are then continuously stirred using magnetic stirrer at 25° C., for 24 hours.

The samples are centrifuged to separate the precipitated amylase at 15,000 rpm for 30 minutes. The precipitated amylase is dissolved in propylene glycol.

The enzyme activity is measured to determine the percent recovery.

Results are shown in table 9.

TABLE 9

| | Percent recovery in precipitate % | |
|---|---|---|
| Metal halide | metal halide example 12 | metal halide + 4-hydroxybenzoic acid methyl ester example 13 |
| KCl | 91.2 | 98.0 |

As shown in table 9, potassium chloride also is effective to precipitate and purify amylase.

EXAMPLES 14 AND 15

These examples illustrate the alpha-amylase precipitation by means of potassium bromide or of sodium bromide and of 4-hydroxybenzoic acid methyl ester.

A concentrated enzyme solution of alpha-amylase from *Bacillus licheniformis* with an activity of 1,000,000 MWU/ml, obtained according to the conditions of the example 1, is prepared.

The pH of the concentrated amylase solution is adjusted to pH 7.6.

To one set of concentrated amylase solution (example 14), sodium bromide is added to a concentration of 2M and 4-hydroxybenzoic acid methyl ester is added to a concentration of 0.12% (w/v). To another set (example 15), potassium bromide is added to a concentration of 2M and 4-hydroxybenzoic acid methyl ester is added to a concentration of 0.12% (w/v).

The samples are then continuously stirred using magnetic stirrer at 25° C. for 24 hours.

The samples are centrifuged to separate the precipitated amylase at 15,000 rpm for 30 minutes. The precipitated amylase is dissolved in propylene glycol.

The enzyme activity is measured to determine the percent recovery.

Results are shown in table 10.

TABLE 10

| Examples | percent recovery in precipitate % |
|---|---|
| 14 | 60.2 |
| 15 | 56.7 |

As shown in table 10, sodium bromide and potassium bromide are also effective to precipitate and purify amylase.

EXAMPLES 16R AND 17R

For Comparison

These examples concern the alpha-amylase precipitation by means of sodium iodide and of potassium iodide.

A concentrated enzyme solution of alpha-amylase from *Bacillus licheniformis* with an activity of 1,000,000 MWU/ml, obtained according to the conditions of the example 1, is prepared.

The pH of the concentrated amylase solution is adjusted to pH 7.6.

To one set of concentrated amylase solution (example 16R), sodium iodide or potassium iodide is added to a concentration of 2M. To another set (example 17R), sodium iodide or potassium iodide is added to a concentration of 2M and 4-hydroxybenzoic acid methyl ester is added to a concentration of 0.12% w/v.

The samples are then continuously stirred using magnetic stirrer at 25° C. for 24 hours.

The samples are centrifuged to separate the precipitated amylase at 15,000 rpm for 30 minutes. The precipitated amylase is dissolved in propylene glycol.

The enzyme activity is measured to determine the percent recovery.

Results are shown in table 11.

TABLE 11

| Metal halide | Percent recovery in precipitate % | |
|---|---|---|
| | example 16R | example 17R |
| NaI | 0 | 0 |
| KI | 0 | 0 |

As shown in table 11, sodium iodide and potassium iodide with or without 4-hydroxybenzoic acid methyl ester are totally ineffective to precipitate and purify amylase.

EXAMPLES 18R AND 19R

For Comparison

These examples concern the alpha-amylase precipitation by means of calcium chloride and of magnesium chloride.

A concentrated enzyme solution of alpha-amylase from *Bacillus licheniformis* with an activity of 1,000,000 MWU/ml, obtained according to the conditions of the example 1, is prepared.

The pH of the concentrated amylase solution is adjusted to pH 7.6.

To one set of concentrated amylase solution (example 18R), calcium chloride or magnesium chloride is added to a concentration of 2M. To another set (example 19R), calcium chloride or magnesium chloride is added to a concentration of 2M and 4-hydroxybenzoic acid methyl ester is added to a concentration of 0.12% w/v.

The samples are then continuously stirred using magnetic stirrer at 25° C. for 24 hours.

The samples are centrifuged to separate the precipitated amylase at 15,000 rpm for 30 minutes. The precipitated amylase is dissolved in propylene glycol.

The enzyme activity is measured to determine the percent recovery.

Results are shown in table 12.

TABLE 12

| Metal halide | Percent recovery in precipitate % | |
|---|---|---|
| | example 18R | example 19R |
| CaCl$_2$ | 0 | 0 |
| MgCl$_2$ | 0 | 0 |

As shown in table 12, calcium chloride and magnesium chloride with or without 4-hydroxybenzoic acid methyl ester are totally ineffective to precipitate and purify amylase.

Of course, it should be understood that a wide range of changes and modifications can be made to the preferred embodiments described above. It is therefore intended that the foregoing detailed description be understood that it is the following claims, including all equivalents, which are intended to define the scope of this invention.

I claim:

1. A method for the preparation of a purified bacterial amylase from a fermentation broth, comprising the following steps:

(i) forming an amylase solution by separating the amylase from cells and suspended solids of said fermentation broth, (ii) concentrating said amylase solution into a concentrated amylase solution, until the enzyme activity of said concentrated amylase solution is at least about 250,000 MWU/ml, (iii) adding a precipitation agent to said concentrated amylase solution in an amount effective to precipitate the amylase, wherein said precipitation agent is a metal halide selected from the group consisting of sodium chloride, potassium chloride, sodium bromide, potassium bromide and a mixture of two or more of these metal halides and adding a further precipitation agent which is an organic compound selected from the group consisting of 4-hydroxybenzoic acid, alkali metal salts of 4-hydroxybenzoic acid, alkyl esters of 4-hydroxybenzoic acid and a mixture of two or more of these organic compounds, (iv) incubating said concentrated amylase solution containing the precipitation agent and the further precipitation agent for a time effective to precipitate the amylase, and (v) collecting a purified amylase precipitate.

2. The method according to claim 1, wherein the metal halide is selected from the group consisting of sodium chloride and potassium chloride.

3. The method according to claim 1, wherein the organic compound is selected from the group consisting of alkali metal salts of 4-hydroxybenzoic acid and linear or branched alkyl esters of 4-hydroxybenzoic acid, wherein the alkyl group contains from 1 to 12 carbon atoms, and a mixture of two or more of these organic compounds.

4. The method according to claim 3, wherein the organic compound is selected from the group consisting of linear alkyl esters of 4-hydroxybenzoic acid, wherein the alkyl group contains from 1 to 6 carbon atoms, and a mixture of two or more of these organic compounds.

5. The method according to claim 4, wherein the organic compound is selected from the group consisting of a methyl ester of 4-hydroxybenzoic acid, a propyl ester of 4-hydroxybenzoic acid and a mixture of these two organic compounds.

6. The method according to claim 1, wherein during the step (iii) at least 5% weight/volume of the metal halide is added to the concentrated amylase solution.

7. The method according to claim 1, wherein during the step (iii) no more than 25% weight/volume of the metal halide is added to the concentrated amylase solution.

8. The method according to claim 1, wherein during the step (iii) at least 0.01% weight/volume of the organic compound is added to the concentrated amylase solution.

9. The method according to claim 1, wherein during the step (iii) no more than 0.3% weight/volume of the organic compound is added to the concentrated amylase solution.

10. The method according to claim 1, wherein the step (iv) is carried out at a pH in a range from about 2.5 pH units below the isoelectric point up to about 2.5 pH units above the isoelectric point of the amylase.

11. The method according to claim 1, wherein the amylase is an alpha-amylase derived from a Bacillus species.

12. The method according to claim 11, wherein the amylase is an alpha-amylase derived from *Bacillus licheniformis*.

13. The method according to claim 12, wherein the step (iv) is carried out at a pH of between about 5.5 and 9.7.

14. The method according to claim 3, wherein the alkali metal salts of the organic compound are selected from the group consisting of sodium or potassium salts of the organic compound.

15. A method for the preparation of a purified amylase, from a fermentation broth, comprising the following steps:
   (i) forming an amylase solution by separating the amylase from cells and suspended solids of said fermentation broth,
   (ii) concentrating said amylase solution into a concentrated amylase solution, until the enzyme activity of said concentrated amylase solution is at least about 250,000 MWU/ml,
   (iii) adding a precipitation agent to said concentrated amylase solution in an amount effective to precipitate the amylase, wherein said precipitation agent is a metal halide selected from the group consisting of sodium chloride, potassium chloride, sodium bromide, potassium bromide and a mixture of two or more of these metal halides and adding a further precipitation agent which is an organic compound selected from the group consisting of 4-hydroxybenzoic acid, alkali metal salts of 4-hydroxybenzoic acid, alkyl esters of 4-hydroxybenzoic acid and a mixture of two or more of these organic compounds,
   (iv) incubating said concentrated amylase solution containing the precipitation agent and the further precipitation agent for a time effective to precipitate the amylase, and
   (v) collecting a purified amylase precipitate.

16. The method according to claim 11, wherein the amylase is an alpha-amylase derived from *Bacillus alcalophilus*.

17. The method according to claim 11, wherein the amylase is an alpha-amylase derived from *Bacillus lentus*.

18. The method according to claim 11, wherein the amylase is an alpha-amylase derived from *Bacillus amyloliquefaciens*.

19. The method according to claim 11, wherein the amylase is an alpha-amylase derived from *Bacillus subtilis*.

20. The method according to claim 11, wherein the amylase is an alpha-amylase derived from *Bacillus stearothermophilus*.

* * * * *

UNITED STATES PATENT AND TRADEMARK OFFICE
CERTIFICATE OF CORRECTION

PATENT NO. : 5,281,526
DATED : January 25, 1994
INVENTOR(S) : Ivan C. Good et al.

It is certified that error appears in the above-indentified patent and that said Letters Patent is hereby corrected as shown below:

Col. 1, line 24, "Bacilli" should be in italics

Col. 2, line 56, "Bacilli" should be in italics

Col. 5, line 57, "seperation" should be "separation"

Col. 9, line 51, Second occurrence of "0.03" should be "0.06"

Col. 9, line 52, after "93.3", change "0.42" to "0.12"

Col. 13, line 12, "KT" should be "KI"

UNITED STATES PATENT AND TRADEMARK OFFICE
CERTIFICATE OF CORRECTION

PATENT NO. : 5,281,526
DATED : January 25, 1994
INVENTOR(S) : Ivan C. Good et al It is certified that error appears in the above-indentified patent and that said Letters Patent is hereby corrected as shown below:

Col. 13, line 21, "For Comparison" should be --(for comparison)--

Col. 14, line 67, "Bacillus" should be in italics

Signed and Sealed this

Twenty-third Day of August, 1994

Attest:

BRUCE LEHMAN

*Attesting Officer*  *Commissioner of Patents and Trademarks*